United States Patent
Lu et al.

(10) Patent No.: US 8,674,289 B2
(45) Date of Patent: Mar. 18, 2014

(54) ISOTOPIC ABUNDANCE IN ATOM TRAP TRACE ANALYSIS

(75) Inventors: Zheng-Tian Lu, Lemont, IL (US); Shiu-Ming Hu, Anhui (CN); Wei Jiang, Lemont, IL (US); Peter Mueller, Lemont (IL)

(73) Assignee: UChicago Argonne LLC, Chicago, IL (US)

( * ) Notice: Subject to any disclaimer, the term of this patent is extended or adjusted under 35 U.S.C. 154(b) by 0 days.

(21) Appl. No.: 13/398,657

(22) Filed: Feb. 16, 2012

(65) Prior Publication Data

US 2013/0214143 A1    Aug. 22, 2013

(51) Int. Cl.
*H05H 3/02* (2006.01)
*H05H 3/00* (2006.01)

(52) U.S. Cl.
CPC ... *H05H 3/02* (2013.01); *H05H 3/00* (2013.01)
USPC .......................................................... 250/251

(58) Field of Classification Search
USPC ...................... 250/251; 204/157.15, 2, 21, 22
See application file for complete search history.

(56) References Cited

U.S. PATENT DOCUMENTS 7,839,450 B2 * 11/2010 Hing .............................. 348/373

OTHER PUBLICATIONS

Du X. et al., "An atom trap system for practical 81Kr dating", Rev. Sci. Instrum. 75, 3224-3232 (2004).*
Jiang et al., "An atom counter for measuring 81Kr and 85Kr in environmental samples", Geochimica et Cosmochimica Acta 91 (2012) 1-6.*
Cheng et al., "An efficient magneto-optical trap of metastable krypton atoms", Review of Scientific Instruments 81, 123106 (2010).*
McKinsey et al., "Radioactive krypton background evaluation using atom counting", Nuclear Instruments and Methods in Physics Research A 545 (2005) 524-531.*
C. Y. Chen et al., "Ultrasensitive Isotope Trace Analysis with a Magneto-Optical Trap", Science 286, 1139 (1999).*
Saey, Paul R.J., "Ultra-low-level Measurements of Argon, Krypton, and Radioxenon for Treaty Verification Purposes", Esarda Bulletin No. 36.*
Reynolds, John H., "High Sensitivity Mass Spectrometer for Noble Gas Analysis", Rev. Sci. Instrum. 27, 928 (1956).*
Alekseev, V. A. et al., "A Pulsed Source for Kr(5s[3/2]1) Resonance State Atoms Using Two-Photon-Driven Amplified Spontaneous Emission: Measurment of Quenching Rate Constants", J. Phys. Chem. A 1999, 103, 4016-4025.*

* cited by examiner

*Primary Examiner* — Robert Kim
*Assistant Examiner* — James Choi
(74) *Attorney, Agent, or Firm* — Foley & Lardner LLP

(57) ABSTRACT

A method and system for detecting ratios and amounts of isotopes of noble gases. The method and system is constructed to be able to measure noble gas isotopes in water and ice, which helps reveal the geological age of the samples and understand their movements. The method and system uses a combination of a cooled discharge source, a beam collimator, a beam slower and magneto-optic trap with a laser to apply resonance frequency energy to the noble gas to be quenched and detected.

13 Claims, 4 Drawing Sheets

US 8,674,289 B2

ISOTOPIC ABUNDANCE IN ATOM TRAP TRACE ANALYSIS

STATEMENT OF GOVERNMENT INTERESTS

The United States government has rights in the invention described herein pursuant to Contract No. DE-ACO2-06CH11357 between the United States Department of Energy and UChicago Argonne, LLC, as operator of Argonne National Laboratory and by National Science Foundation, Division of Earth Sciences, under Award No. EAR-0651161.

BACKGROUND OF THE INVENTION

The invention relates to methods and systems for detecting selected isotopes of all noble gases. More particularly, the invention is directed to methods and systems for performing atomic counting based on the atom trap trace analysis method ("ATTA") to measure ratios of $^{81}$Kr/Kr and $^{85}$Kr/Kr in environmental samples.

Krypton permeates through the atmosphere at a concentration of about one part per million. There are six stable Kr isotopes, and two rare, long-lived isotopes: $^{81}$Kr($t_{1/2}$=2.29× $10^5$ yr, isotopic abundance $^{81}$Kr/Kr=6×10$^{-13}$) and $^{85}$Kr ($t_{1/2}$=10 yr, $^{85}$Kr/Kr~10$^{-11}$). Upon the discovery of $^{81}$Kr in the atmosphere, it has been proposed that $^{81}$Kr is an ideal tracer isotope for dating water and ice in the age range of $10^5$-$10^6$ years, a range beyond the reach of $^{14}$C-dating. $^{81}$Kr is mainly produced in the upper atmosphere by cosmic-ray induced spallation and neutron activation of stable Kr. Due to its long residence time, $^{81}$Kr is expected to be distributed uniformly throughout the atmosphere. Subsurface sources and sinks for $^{81}$Kr other than radioactive decay are most likely negligible. Human activities involving nuclear fission have a negligible effect on the $^{81}$Kr concentration because the stable $^{81}$Br shields $^{81}$Kr from the decay of the neutron-rich fission products. All of these favorable conditions combine to support the case for $^{81}$Kr-dating. The other long-lived krypton isotope, $^{85}$Kr, has a completely different production source. It is a fission product of $^{235}$U and $^{239}$Pu, and is released into the atmosphere primarily by nuclear fuel reprocessing activities. $^{85}$Kr can be used as a tracer to study air and ocean currents, determine residence time of young groundwater in shallow aquifers and monitor nuclear fuel processing activities.

For $^{85}$Kr analysis, low level decay counting (LLC) is performed routinely in a few specialized laboratories around the world. LLC was also the first method used to detect $^{81}$Kr and to determine its abundance in the atmosphere, but it is too inefficient for practical $^{81}$Kr-dating because only a fraction 3×10$^{-8}$ of $^{81}$Kr atoms in a sample decays in a 100-hour measurement. In general, counting atoms is preferable to counting decays for analyses of long-lived isotopes because of the enhanced efficiency, and because of the immunity to other decay backgrounds from both the sample and the surroundings. An accelerator mass spectrometry (AMS) method for counting $^{81}$Kr ions has been developed, and has been used to perform $^{81}$Kr-dating of four groundwater samples from the Great Artesian Basin of Australia. However, due to the complexity of this technique, which required the use of a high energy (4 GeV) cyclotron to produce fully stripped $^{81}$Kr ions, and the large sample size required (16 tons of water), the AMS effort on $^{81}$Kr-dating was halted following these proof-of-principle measurements.

Atom Trap Trace Analysis (ATTA) is another type of atom-counting method capable of detecting both $^{81}$Kr and $^{85}$Kr in environmental samples. In ATTA, an atom of a particular isotope is selectively captured by resonant laser light in a magneto-optical trap (MOT) and detected by observing its fluorescence. Following the first demonstration of ATTA, both the reliability and counting efficiency of the ATTA instrument have been improved. An earlier version, ATTA-2, had a counting efficiency of 1×10$^{-4}$ and, for each $^{81}$Kr/Kr analysis, needed a sample of 50 µL STP of Kr gas extracted from approximately 1000 kg of water. The ATTA-2 instrument had a limited dynamic range: it could only be used to count the rare $^{81,85}$Kr isotopes, not the abundant stable isotopes, for example, $^{83}$Kr whose isotopic abundance is 11.5%. The isotopic abundance $^{81}$Kr/Kr had to be measured in two steps: first, a controlled amount of $^{85}$Kr was introduced into the sample and its $^{85}$Kr/Kr ratio was determined with LLC; second, ATTA-2 was used to measure $^{81}$Kr/$^{85}$Kr. The two ratios were then combined to obtain $^{81}$Kr/Kr. Despite its dependence on additional measurements with other techniques and the relatively large sample size required, ATTA-2 was used successfully for $^{81}$Kr-dating of old groundwater of the Nubian aquifer in western Egypt. However, none of these prior art methods and systems, including the existing ATTA-2 systems have enabled efficient or commercially practical methods and systems for detection and analysis of $^{81}$Kr/Kr or $^{85}$Kr/Kr ratios. Consequently, there is a substantial need for a commercially efficient method for Kr isotope measurements and analysis.

SUMMARY OF THE INVENTION

An efficient and selective atom counter (ATTA-3) system and method based on this Atom Trap Trace Analysis (ATTA) method has been developed to measure both $^{81}$Kr/Kr and $^{85}$Kr/Kr ratios of environmental samples in the range of $10^{-14}$-$10^{-10}$. Compared to the previously reported ATTA-2 instrument, the counting rates of ATTA-3 are higher by two orders of magnitude and the required sample size lower by one order of magnitude. For $^{81}$Kr dating in the age range of 200-1,500 kyr, the required sample size is 5-10 µL STP of krypton gas, which can be extracted from approximately 100-200 kg of water or 40-80 kg of ice. Moreover, a laser-induced quenching scheme was developed to enable measurements of the trap capture rates of both the rare $^{81,85}$Kr and the abundant $^{83}$Kr, whose isotopic abundances differ by 11 orders of magnitude. This scheme allows the ATTA-3 system to directly determine $^{81}$Kr/Kr and $^{85}$Kr/Kr ratios without other supplemental measurements. ATTA-3 represents a highly effective and commercially efficient method and system for routine analysis of these rare noble gas tracers Now for the first time, $^{81}$Kr-dating is available for commercial use and used by the earth science community at large. It should also be appreciated that the described ATTA-3 can also be used to analyze other noble gas isotopes, for example, $^{39}$Ar.

These and other advantages and features of the invention, together with the organization and manner of operation thereof, will become apparent from the following Detailed Description when taken in conjunction with the accompanying drawings described below.

Figure 3A:
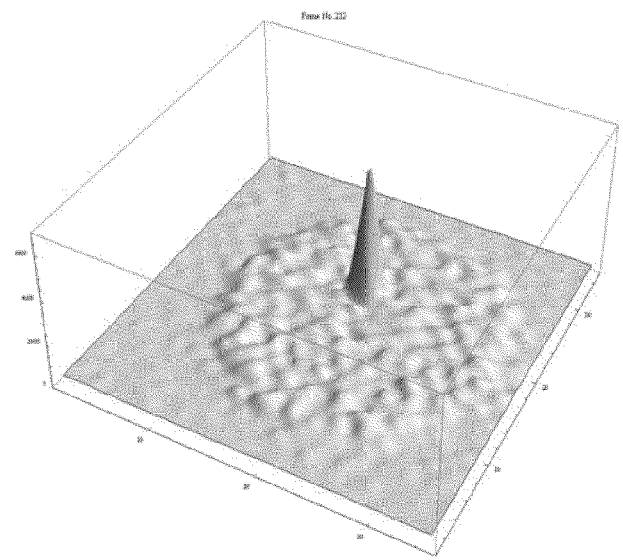
Figure 3B:
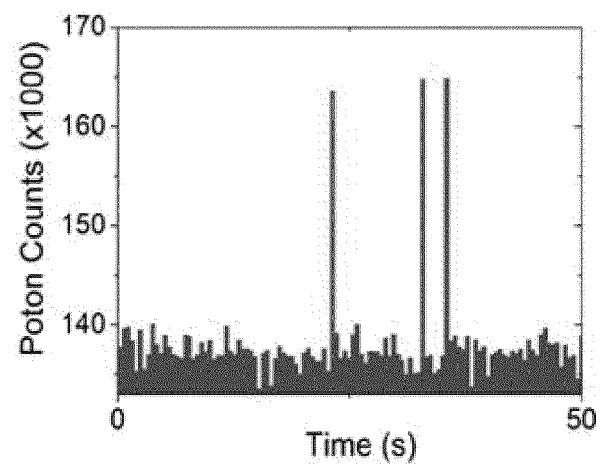

$2]_2$ is excited to quench the metastable $^{83}$Kr atoms, and the $5s[3/2]_1$-$5p[5/2]_2$ fluorescence is detected for $^{83}$Kr measurements;

FIG. 3 shows the detection of single $^{81}$Kr atoms in the trap. (a) the fluorescence image of a single $^{81}$Kr atom in the trap as recorded by the CCD camera. (b) photon counts integrated over a region-of-interest on the CCD image shows discrete steps as individual atoms are captured by or lost from the trap.

Figure 4:
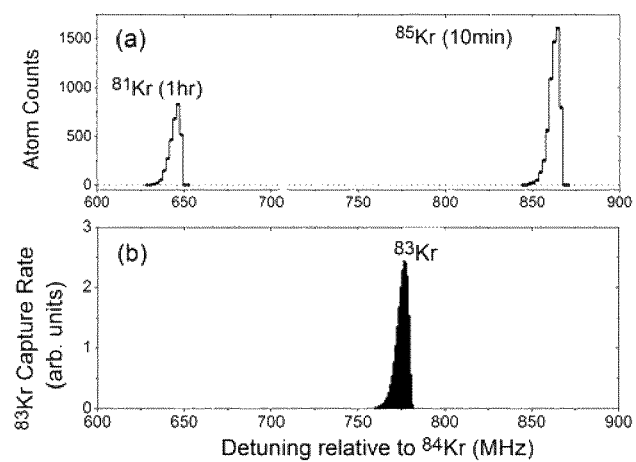

FIGS. 4(a)-(b) show trap capture rate versus laser frequency detuning. (a) The integration time for each data point of the $^{81}$Kr peak is one hour, and 10 minutes for $^{85}$Kr. The atom is detected by collecting the 811 nm fluorescence on the cycling transition. Zero atom counts on both sides of peaks illustrate the immunity of ATTA to any contamination by other species. (b) For $^{83}$Kr, 878 nm fluorescence is recorded in the laser induced quenching procedure (see text for details).

Figure 5:
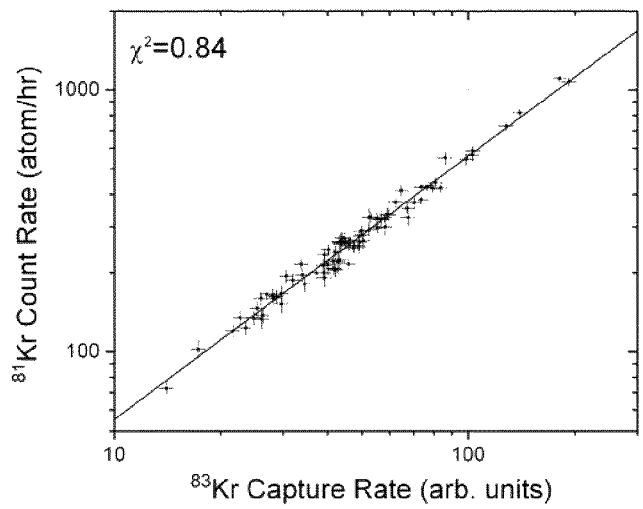
Figure 6:
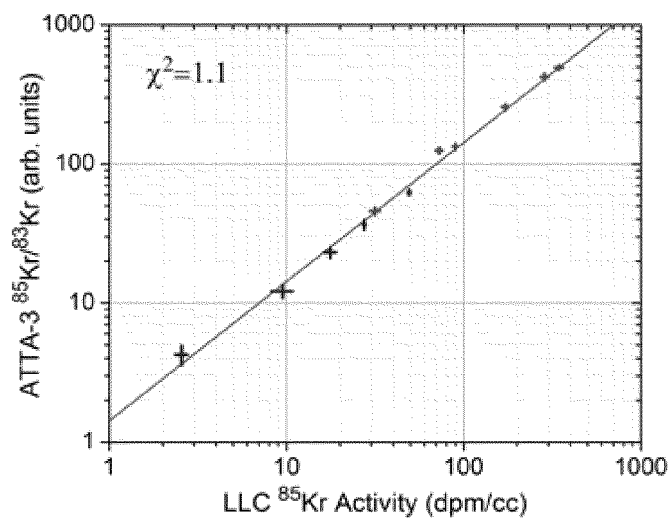

FIG. 5 shows comparison of the atom capture rates between the rare $^{81}$Kr and abundant $^{83}$Kr for a single test sample under a variety of trapping conditions; the linearity of the fit demonstrates that the 878 nm signal can be used effectively for normalizing the $^{81}$Kr/Kr (or $^{85}$Kr/Kr) ratio measurements;

FIG. 6 shows comparison of $^{85}$Kr/Kr ratios measured by ATTA-3 and LLC. ATTA-3 measures the $^{85}$Kr/$^{83}$Kr ratio in arbitrary units. LLC measures the $^{85}$Kr decay activity in the units of decays per minute per cc-STP of krypton gas (dpm/cc); six samples (blue data points) were measured in a blind arrangement—the ATTA-3 and LLC results were only revealed and compared after the measurements had completed; in addition to the points shown in this figure, a sample with $^{85}$Kr below the LLC detection limit was also analyzed: LLC, $^{85}$Kr activity <1 dpm/cc; ATTA-3, $^{85}$Kr/$^{83}$Kr <2.0 (90% C.L.). ATTA-3 and LLC results agree at the +7% level (chi-square=1.1); and FIG. 7. shows sample size vs sample age and desired accuracy for $^{81}$Kr-dating; the two curves are for a relative age error off 10% and ±20%, respectively.

DETAILED DESCRIPTION OF THE PREFERRED EMBODIMENTS

Figure 1:
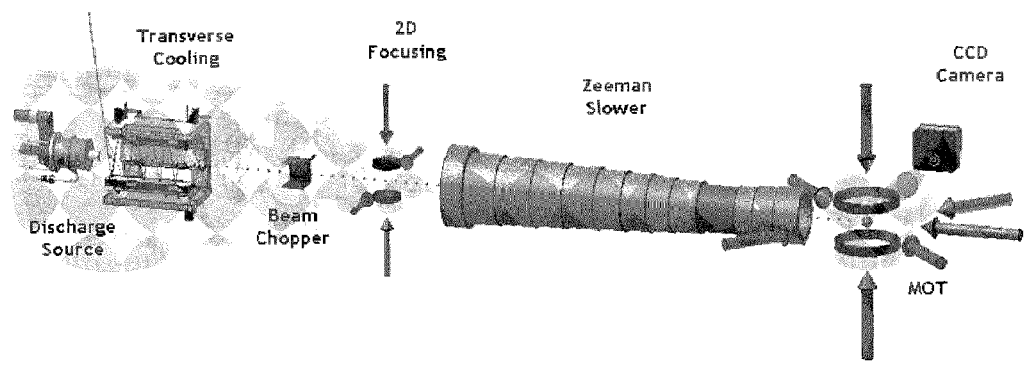
FIG. 1 shows a schematic of the ATTA-3 apparatus of the invention; the total length of the atomic beamline is approximately 2 m. lasers and optics are located on an adjacent laser table of a similar length.
Figure 2:
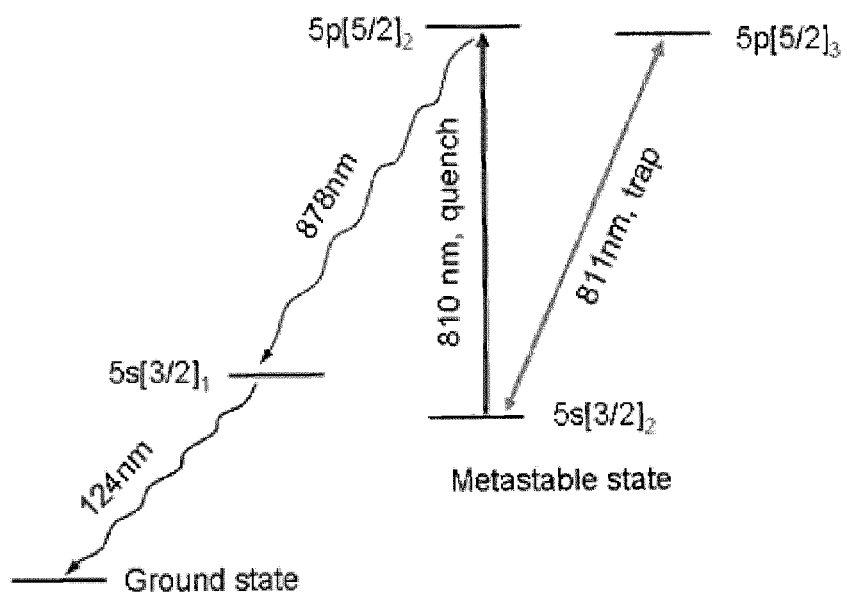
FIG. 2 shows an atomic level diagram of Kr; the 5s[3/2]$_2$ state is metastable and the cycling transition 5s[3/2]$_2$-5p[5/2]$_3$ is excited for trapping and its fluorescence detected for single atom counting of $^{81,85}$Kr; the transition 5s[3/2]$_2$-5p[5/

An ATTA system 100 constructed in accordance with a method and system of the invention is shown in FIG. 1. In the method of the invention laser trapping and cooling of Kr atoms are achieved by the resonant excitation of the cycling transition $5s[3/2]_2$-$5p[5/2]_3$ (see FIG. 2). This $5s[3/2]_2$ state is metastable, and is populated with an efficiency of $10^{-4}$ by sending the sample gas through a RF-driven discharge source. A newly developed discharge source 110 is cooled by a liquid nitrogen reservoir (not shown), resulting in a slower beam of atoms 115 and a gain by a factor of two in the trapping efficiency. A diverging beam 120 of metastable atoms is collimated in a 20 cm long, two-dimensional transverse cooling zone 130. The forward atomic beam flux is enhanced by a factor of one hundred forty, resulting in a gain by a factor of two over the prior art ATTA-2 method. A mechanical beam chopper 135 is used to periodically turn on the atomic beam in the capture phase and to turn it off in the detection phase. A two-dimensional MOT type of trap 150 is installed in the system 100 to focus the already collimated atomic beam, thus boosting the trap capture efficiency by a factor of three. A new Zeeman slower 140, containing a reverse-biased segment near the MOT 150, improves the transition of atoms from the slower into the MOT trap 150, and improves the trapping efficiency by a factor of three. In addition, a factor of three increase in laser power (a total of 2 W) and complete sideband coverage for hyperfine repumping improve the trapping efficiency by a factor of four.

Analyzing an atmospheric Kr sample, the system 100 can capture $^{83}$Kr (11.5%) atoms at the rate of $\sim 1 \times 10^{11}$ s$^{-1}$, $^{81}$Kr ($6 \times 10^{-13}$) at the rate of 1,000 per hour and $^{85}$Kr ($10^{-11}$) at 20,000 per hour. This represents a combined improvement by two orders of magnitude over the previously reported prior art ATTA-2 results. Further, instead of an avalanche photodiode employed in ATTA-2, a sensitive EMCCD camera 160 is used in the system 100 to image the fluorescence of the trapped atom. The described examples utilized a Luca S EMCCD camera made by Andor Technology A single Kr atom in the trap is repeatedly excited on the $5s[3/2]_2$-$5p[5/2]_3$ transition by the resonant trapping laser beams at 811 nm (see FIG. 2). The atom absorbs and emits photons at the rate of $1 \times 10^7$ s$^{-1}$, of which 1% of the fluorescence photons are collected by an imaging lens onto the camera. By providing the spatial as well as the intensity information, the camera image (see FIG. 3a) makes it easier and more reliable to align the single trap. A circular region of interest is defined on the camera image, within which the photon counts are integrated to form a signal of the atom (see FIG. 3b). Background photon counts are caused by both the laser light scattered off walls and the dark counts of the camera. Under the optimum conditions, the signal-to-noise ratio of a single trapped atom is approximately twenty. The threshold for single atom detection is set at seven standard deviations above background.

The system 100 is immune to interference from any other isotope, element, or molecule. When the laser frequency is tuned to the resonance of the desired isotope, $^{81}$Kr or $^{85}$Kr, only atoms of this specific isotope are trapped (see FIG. 4a). Other species are either deflected before reaching the MOT 150 or are allowed to pass through it without being captured. Indeed, the number of atom counts drops to zero on both sides of the $^{81}$Kr or $^{85}$Kr peak. There is no interference from counts due to the nearby peak of $^{83}$Kr (see FIG. 4b), an isotope that is more abundant by 11 orders of magnitude. This superb selectivity is due to two characteristics of the MOT 150: resonance and repetition—laser trapping works only when the atom resonantly and repeatedly scatters photons at the rate of $10^7$ per second.

Compared to single-atom counting of $^{81}$Kr or $^{85}$Kr, an accurate determination of the trap capture rate of the abundant isotope $^{83}$Kr is surprisingly difficult, yet it is required in order to measure the isotopic abundances of $^{81}$Kr/Kr and $^{85}$Kr/Kr. Here, we assume that the $^{83}$Kr/Kr ratio (=11.5%) is a constant throughout the near-surface Earth environment. Interaction among the large number ($10^9$) of $^{83}$Kr atoms in the trap causes loss of atoms due to ionization, quenching, and other forms of inelastic collisions. Consequently, the average time for an atom to stay in the MOT 150, the so-called trap lifetime, depends sharply on the number and the density of atoms in the MOT 150, and is difficult to control and determine to the required accuracy (±5%). Since the fluorescence signal of the cycling transition at 811 nm from the trapped $^{83}$Kr atoms is proportional to the trap lifetime—the longer an atom stays in the MOT 150, the more fluorescence photons at 811 nm it emits—the large uncertainty in determining the MOT 150 lifetime causes a similar difficulty in accurately determining the capture rate of $^{83}$Kr. This is not a problem for counting the rare $^{81,85}$Kr isotope. For one, the number of trapped $^{81,85}$Kr atoms is small, and their trap lifetime is long (1 s) and stable. In addition, the signal size of the 811 nm fluorescence is discrete when there are only a couple of $^{81,85}$Kr atoms in the MOT 150, making atom counting of $^{81,85}$Kr possible without knowing the trap lifetime.

In prior art ATTA-2 system, this problem was bypassed by injecting a known amount of $^{85}$Kr into the sample being analyzed and using $^{85}$Kr as a control isotope for $^{81}$Kr measurement, and vice versa. This procedure introduced additional complexity and potential sources of errors into the final age determination. The system 100 has succeeded in measuring the capture rate of $^{83}$Kr accurately with a laser-induced quenching procedure. A 200 µW laser beam of 810 nm is directed at the trapped atoms to resonantly excite the 5s[3/2]$_2$-5p[5/2]$_2$ transition (see FIG. 2). An atom excited to the 5p[5/2]$_2$ state decays to the ground state through the intermediate 5s[3/2]$_1$ state, emitting two photons at 878 nm and 124 nm, respectively. Once in the ground state, the atom no longer interacts resonantly with the laser beams and is lost from the trap. This quenching process actively reduces the lifetime and, thus, reduces the number of $^{83}$Kr atoms in the MOT 150 by one order of magnitude while the collisional loss rate is reduced by two orders. While the 811 nm fluorescence of the cycling transition is proportional to the trap lifetime, the 878 nm fluorescence is not. Instead, each $^{83}$Kr atom in the trap emits a single 878 nm photon before dropping to the ground state. The fluorescence at 878 nm, although much weaker, is linearly proportional to the rate of atoms being captured by the trap, and is insensitive to any drifts of laser power and frequency. Detecting the 878 nm fluorescence of $^{83}$Kr induced by the quenching laser beam, we have measured both the $^{81}$Kr/$^{83}$Kr and $^{85}$Kr/$^{83}$Kr ratios of a single test sample under a variety of trapping conditions and overall capture rates (see FIG. 5), and found these ratios to remain constant within the statistical uncertainty of ±9% for $^{81}$Kr/$^{83}$Kr and ±7% for $^{85}$Kr/$^{83}$Kr. This new procedure is adopted in the system 100 for all isotope ratio measurements.

Cross-sample contamination is one limitation on the sample size requirement and sample processing time of the system 100. While the discharge is used to excite the Kr atoms to the metastable 5s[3/2]$_2$ state, it also ionizes the atoms and implants them into the surrounding walls, thus causing a slow loss of the sample. Later on, under the bombardment of the energetic ions, those embedded atoms of the current and previous samples can be slowly released back into the vacuum system. Over time, atoms from previous samples slowly accumulate in the system 100, causing an instrumental memory effect. This effect is mitigated by flushing the system 100 for 36 hours with a xenon gas discharge between measurements. During flushing, the outgassing rate of Kr is recorded with a residual gas analyzer, and is observed to drop by two orders of magnitude down to an acceptable level of 0.015 µL STP per hour. In addition, both the $^{81}$Kr/Kr and $^{85}$Kr/Kr ratios of the outgassing Kr can be measured directly with atom counting. Although the contamination is small compared to the sample size of 5-10 µL, it is not entirely negligible, particularly when a sample is old and the $^{81}$Kr/Kr abundance is much lower than that of the contaminant from previous samples. Since both the release rate and the $^{81}$Kr/Kr abundance of the contaminant can be determined, a correction is made and its associated error is added to the result of each sample. In the future, this limitation may be removed by replacing the discharge source of metastable atoms with a photon excitation scheme.

The following non-limiting Example illustrates various aspects of the invention.

Example

The $^{85}$Kr/Kr ratios measured at Argonne National Laboratory with the system 100 were compared to those measured independently at the University of Bern with LLC. A total of 12 Kr samples were prepared in Bern by mixing varying amounts of modern atmospheric Kr with a Kr sample originally taken from air prior to the dawn of the nuclear age containing basically zero $^{85}$Kr concentration. The resulting $^{85}$Kr/Kr ratios among these samples varies from 0 to $1 \times 10^{-10}$. These ratios were determined both by the volume mixing ratios and by LLC of $^{85}$Kr. The $^{81}$Kr/Kr ratios are expected to remain constant among all these samples. Using the system 100, both the $^{85}$Kr/Kr and $^{81}$Kr/Kr ratios were measured several times for each sample, with each measurement consuming approximately 10 STP of Kr. During a measurement, the laser frequency was switched among $^{81}$Kr, $^{83}$Kr, and $^{85}$Kr every few minutes to average out any drifts in trapping and detection efficiencies. The final isotope ratio results, after correction for the memory effect, are displayed in FIG. 6. The system 100 and LLC measurements agree on the $^{85}$Kr/Kr ratios at the ±7% level (chi-square=1.1). Moreover, the $^{81}$Kr/Kr ratios measured with ATTA-3 indeed remain constant at the ±9% level (chi-square=1.0). We note that the system 100 does not directly measure absolute isotope ratios. Instead, the measured ratios of unknown samples are normalized to those of a standard reference, for this example a well-studied atmospheric krypton sample. 2×2×. It should be appreciated that other samples can be utilized as a standard reference.

Figure 7:
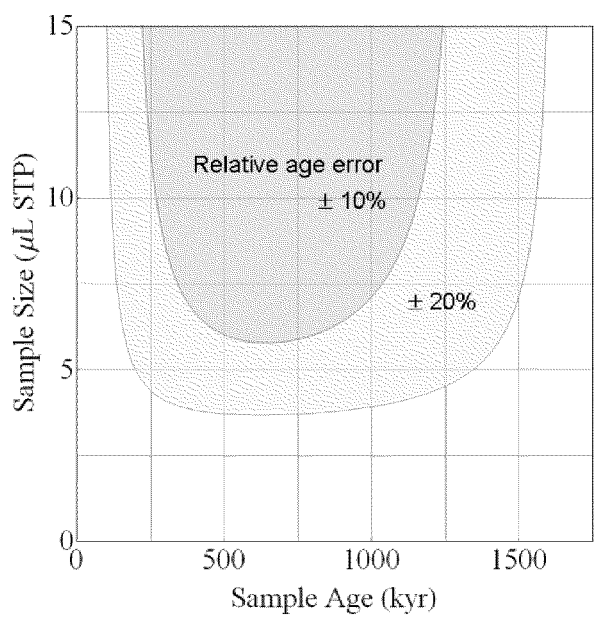

The required sample size for applications in $^{81}$Kr-dating depends on both the sample age and the desired uncertainty in age determination (see FIG. 7). $^{81}$Kr-dating with the system 100 covers an effective age range from 150 kyr to 1.5 Myr, or 0.6-6 times the half-life of the isotope. On the side younger than 150 kyr, the change of $^{81}$Kr/Kr is too small to provide adequate age resolution. On the side older than 1.5 Myr, the $^{81}$Kr/Kr ratio itself is too small compared to the error introduced by the correction for the memory effect. Within the effective age range, a typical sample size is 5-10 µL STP of Kr gas, which can be extracted from approximately 100-200 kg of water or 40-80 kg of ice. It should be noted that these are not absolute requirements; rather, they should be viewed as a guideline. If needed, extraordinary steps, for example prolonged xenon flushing in order to reduce the memory effect, can be taken to further reduce the required sample size and meet the special demands of a particular application. The chemical purity of the krypton sample is not important since the ATTA method is immune to contamination from any other species.

The foregoing description of embodiments of the present invention have been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

The invention claimed is:

1. A method of measuring noble gas isotopes in a sample, comprising the steps of:
   providing a source of noble gas isotopes;
   providing a discharge source for providing a beam of metastable atoms;
   collimating the beam of atoms;
   selectively actuating a beam chopper for chopping the beam of atoms;
   providing a beam slower for enhancing beam trapping efficiency;

detecting the metastable atoms in magneto-optical trap, thereby detecting the noble gas isotope present in the beam of atoms; and flushing out noble gas isotopes embedded in surrounding system walls by discharging Xe gas in the system between measuring steps for noble gas isotopes.

2. The method as defined in claim 1 wherein the discharge source comprises a liquid $N_2$ cooled RF discharge source, thereby providing a slower beam of atoms for analysis.

3. The method as defined in claim 1 wherein the collimating of the beam of atoms includes a two-dimensional transverse cooling step.

4. The method as defined in claim 1 wherein the beam chopper is activated in an atom capture phase and turned off in an atom beam detection phase.

5. The method as defined in claim 1 wherein the step of detecting utilizes the step of detecting utilizes a two-dimensional mageto-optical trap.

6. The method as defined in claim 1 further including the step of providing a laser for resonant laser trapping of the noble gas isotope.

7. The method as defined in claim 1 wherein the step of detecting is performed by a CCD camera.

8. The method as defined in claim 1 wherein the noble gas isotope consists of at least one of $^{81}Kr/Kr$ and $^{85}Kr/Kr$.

9. The method as defined in claim 8 wherein the noble gas isotopes further include $^{83}Kr$ and a portion of the $^{83}Kr$ is in a ground state and is lost from the magneto-optical trap, thereby enabling measurement of $^{81}Kr/^{83}Kr$ and $^{85}Kr/^{83}Kr$.

10. The method as defined in claim 1 wherein the step of detecting includes setting and applying a laser beam to resonance frequencies of the noble gas isotope.

11. The method as defined in claim 1 wherein the noble gas resides in ice or water, thereby enabling dating of water and ice.

12. The method as described in claim 1 wherein the step of detecting includes a laser-induced quenching procedure to accurately measure the capture rate of an abundant noble gas isotope.

13. A system for measuring noble gas isotopes in a sample, comprising:
 a discharge source for providing a beam of atoms containing the noble gas isotopes;
 a beam chopper for selectively activating and deactivating to use with the beam of atoms;
 a beam slower;
 including a Xe gas source and discharge component to provide a Xe gas discharge in the system;
 a magneto-optic trap including a laser beam for applying resonant energy to the noble gas isotopes for trapping and analyzing the noble gas isotopes; and
 a quenching laser system.

* * * * *